United States Patent [19]

Hayashi et al.

[11] Patent Number: 5,659,043

[45] Date of Patent: Aug. 19, 1997

[54] THIOL COMPOUNDS

[75] Inventors: Kazuhiko Hayashi, Iruma-gun; Chisato Sato, Kamifukuoka; Satoshi Tamai, Kawasaki, all of Japan

[73] Assignee: Lederle (Japan) Ltd., Tokyo, Japan

[21] Appl. No.: 570,888

[22] Filed: Dec. 12, 1995

[30] Foreign Application Priority Data

Dec. 12, 1994 [JP] Japan .................................. 6-331423
Sep. 11, 1995 [JP] Japan .................................. 7-257281

[51] Int. Cl.$^6$ .................................................. C07D 417/04
[52] U.S. Cl. .......................................... 548/193; 540/350
[58] Field of Search ............................................ 548/193

[56] References Cited

U.S. PATENT DOCUMENTS 5,534,510  7/1996  Abe .............................. 514/210

FOREIGN PATENT DOCUMENTS 0 632 039  1/1995  European Pat. Off. .

OTHER PUBLICATIONS

Chem. Bull Chem Soc. Japan 41 (3) 712 (1968).

*Primary Examiner*—Robert Gerstl
*Attorney, Agent, or Firm*—Foley & Lardner

[57] ABSTRACT

This invention relates to 3-mercapto-1-(1,3-thiazolin-2-yl) azetidine represented by the following formula and its acid addition salts

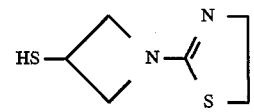

and to the production process therefor. The above compounds are useful as intermediates for preparing carbapenem compounds, which have strong antibacterial activity, with convenience and high yield.

2 Claims, No Drawings

THIOL COMPOUNDS

The present invention relates to thiol compounds, and, more detailedly, to novel thiol compounds which are useful as synthesis intermediates for a certain kind of orally administrable carbapenem compound which shows strong antibacterial activity, and to acid addition salts of said thiol compounds, and further to the processes for the production of these compounds, and, moreover, to novel synthesis intermediates which are useful in said production processes.

There have heretofore been found out a lot of compounds having what is called a carbapenem skeleton, and, from among such compounds, there have been proposed some ones having excellent antibacterial activity. On account of their low absorbability from alimentary canal, however, most of the carbapenem compounds which have so far been proposed are clinically thought to be administered as injections only.

In view of the purpose of therapy or circumstances on the side of patients, it is desirable in clinical practice that several dosage routes can be selected for the administration of medicines. Compared with injections, oral drugs are especially preferable and clinically quite useful since they can be administered easily and conveniently, and since they can be administered also in one's own home.

Clinically, therefore, there have been strong demands for the development of carbapenem compounds which have a wide range of antibacterial spectrum and strong antibacterial activity and which can orally be administered.

Under the above-mentioned circumstances, the authors of this invention made studies over and over again about orally administrable carbapenem compounds, and found that compounds which have, as a substituent at the 2-position of carbapenem skeleton, a 1-(1,3-thiazolin-2-yl)azetidin-3-ylthio group represented by the following formula (X)

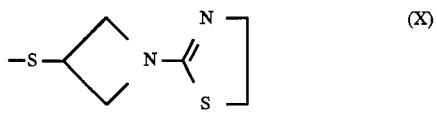

or, typically, such a carbapenem compound as is represented by the following formula (IX)

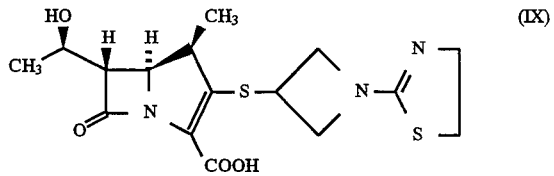

exhibits per se high antibacterial activity, and that, moreover, an ester derivative which is prepared by esterifying the carboxyl group at 3-position of the above compound with a specific ester residue has excellent absorbability from alimentary canal and, besides, is converted again to the compound of the above formula (IX) when rapidly hydrolyzed in vivo, and thus found that, therefore, the above-mentioned ester derivative can be used as a clinically excellent antibacterial agent, especially, for oral administration, in the form of a prodrug of the compound of the above formula (IX), and, thus, they have already applied for a patent with regard to the compound of the above formula (IX) and their ester derivatives (Japanese Patent Application No. 6-170496; U.S. patent application Ser. No. 8/267397; EP-A-632039 etc.).

The main object of the present invention is to provide a synthesis intermediate for the purpose of efficiently introducing a 1-(1,3-thiazolin-2-yl)-azetidin-3-ylthio group represented by the above formula (X), which is a characteristic substituent at the 2-position of the compounds of the above formula (IX), into a carbapenem skeleton.

The other objects of this invention will be seen clearly from the following description:

This invention provides 3-mercapto-1-(1,3-thiazolin-2-yl)azetidine which is represented by the following formula (I) and its acid addition salts:

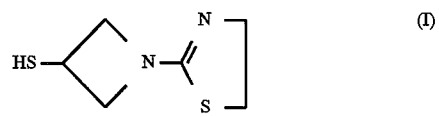

The compound which is represented by the above formula (I) and its acid addition salts are quite useful as key intermediate s for the industrial-scale efficient production of the clinically quite useful carbapenem compound represented by the above formula (IX) which exhibits per se high antibacterial activity, and which becomes orally administrable when esterified.

Examples of the acid addition salts of the compound of the above formula (I) include addition salts with organic acids like lower aliphatic acids such as acetic acid, propionic acid, butyric acid, trifluoroacetic acid and trichloroacetic acid; substituted or unsubstituted benzoic acids such as benzoic acid and p-nitrobenzoic acid; (halo)lower alkylsulfonic acids such as methanesulfonic acid and trifluoromethanesulfonic acid; substituted or unsubstituted aryl sulfonic acids such as benzenesulfonic acid, p-nitrobenzenesulfonic acid, p-bromobenzenesulfonic acid, toluenesulfonic acid and 2,4,6-triisopropylbenzenesulfonic acid; and organic phosphoric acids such as diphenylphosphoric acid; as well as addition salts with inorganic acids like hydrochoric acid, sulfuric acid, hydrobromic acid, hydroiodic acid, fluoroboric acid, perchloric acid and nitrous acid.

The compound of the above formula (I) can be efficiently produced by any of the following three characteristic processes A, B and C, for example:

Process variant A:

In this process, the compound of the above formula (I) is produced from 2-halomethyl aziridine as a starting material by the path shown in the following reaction scheme (A):

Scheme (A)

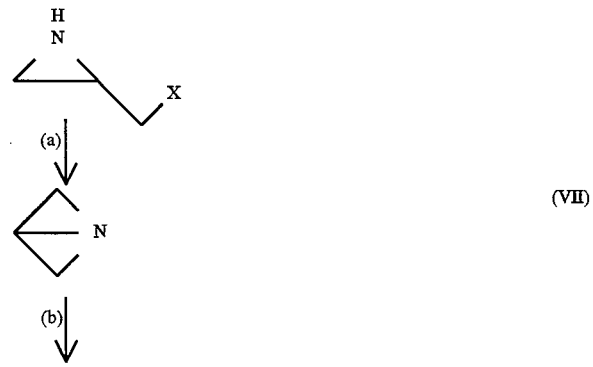

-continued
Scheme (A)

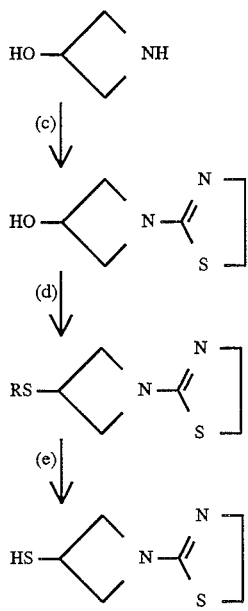

In the above formulae, R denotes an acyl group, a substituted or unsubstituted lower alkyl group or an aryl group; and X denotes a halogen atom.

In this specification, the term "lower" means that the number of the carbon atoms to which this term is attached is six or less, preferably four or less.

"Lower alkyl group" may be either straight-chain one or branched-chain one. Examples thereof include methyl, ethyl, n-propyl, isopropyl, n-butyl, isobutyl, sec-butyl, tert-butyl, n-pentyl, isopentyl, n-hexyl, isohexyl, n-heptyl and isoheptyl. Preferable among them are methyl, ethyl, n-propyl, isopropyl, n-butyl, isobutyl, sec-butyl and tert-butyl. Under circumstances, these lower alkyl groups may be substituted with a phenyl group which may further be substituted with at least one, preferably one or two, substituent which is selected from the group consisting of hydroxy, methoxy, acetoxy and nitro.

"Acyl group" may be such one as is left after hydroxyl group is removed from the carboxyl portion of organic carboxylic acids. Examples of acyl groups include lower alkanoyl groups such as acetyl, propionyl and butyryl, or a substituted or unsubstituted benzoyl group.

"Aryl group" may be monocyclic or polycyclic, and, further, may have one or more substituent such as lower alkyl group, nitro group and halogen atom on its ring. Examples of aryl group include phenyl, tolyl, xylyl, α-naphtyl and β-naphtyl groups.

"Halogen atom" includes fluorine, chlorine, bromine and iodine atoms, and, among these, chlorine, bromine and iodine atoms are preferable.

In the following, the method shown by Scheme (A) is minutely explained in accordance with each step:

Step (a)

In this step, 2-halomethyl aziridine is made to react with a base, and, thus, is converted into 1-azabycyclo[1.1.0.]butane which is represented by formula (VII).

The above reaction is conducted as follows: 2-halomethyl aziridine is dissolved or suspended in a reactionally inert solvent selected from among alcohol type solvent such as methanol, ethanol, propanol and n-butanol; ether type solvent such as diethyl ether and tetrahydrofuran; hydrocarbon type solvent such as n-heptane, n-hexane, cyclohexane, penfane and cyclopentane; ester type solvent such as methyl acetate ester and ethyl acetate ester; halogen type solvent such as dichloromethane, chloroform and carbontetrachloride; or acetonitrile, dimethylformamide, dimethylacetamide, dimethylsulfoxide and the like; preferably, ether type solvent such as diethyl ether and tetrahydrofuran, and, to the resultant solution or suspension, there are added suitable bases selected from organic and inorganic bases like alkaline metals such as lithium, sodium and potassium; alkaline earth metals such as calcium and magnesium; alkaline metal hydrides such as lithium hydride and sodium hydride; alkaline earth metal hydrides such as calcium hydride; alkaline metal hydroxides such as sodium hydroxide and potassium hydroxide; alkaline metal carbonates such as sodium carbonate and potassium carbonate; alkaline metal hydrogencarbonates such as sodium hydrogencarbonate and potassium hydrogencarbonate; alkaline metal alkyls such as methyllithium and n-butyllithium; alkyl Grignard reagents; alkaline metal amides such as lithiumamide, lithiumdiisopropylamide, sodiumamide and potassiumamide; alkaline metal alkoxides such as sodiummethoxide, sodiumethoxide and potassium tertiary butoxide; alkaline metal alkanoates such as sodium acetate; alkaline earth metal carbonates such as magnesium carbonate and calcium carbonate; tri(lower)alkylamine such as trimethylamine, triethylamine, N,N-diisopropyl-N-ethylamine; pyridine compounds such as pyridine, picoline, lutidine, N,N-di(lower)alkylaminopyridine like N,N-dimethylaminopyridine; quinolines; N-(lower)alkylmorpholine such as N-methylmorpholine; N,N-di(lower)alkyl benzylamine such as N,N-dimethylbenzylamine; and DMSO salts which are made from DMSO and sodium hydride or lithium hydride; preferably, alkyl lithium such as methyl lithium and n-butyllithium, and alkaline metal amides such as lithium amide and lithium diisopropylamide, and, then, the resultant mixture is stirred.

The amount of the above bases used in this reaction is not especially restricted. Usually, the bases are used at the proportion of about 1 to about 20 moles, preferably about 1.5 to about 5 moles, per mole of 2-halomethylaziridine. The reaction temperature is not strictly limited, and may be adequately changed according to the species and amount of the bases used. Usually, the reaction is suitably carried out at the temperature in the range of about −78° C. to about 100° C., preferably about −78° C. to about 60° C., and, under such conditions, the reaction can be completed in about 10 minutes to several days.

The reaction is preferably conducted in the stream of inert gas such as nitrogen or argon gas.

The above-mentioned step gives the compound of formula (VII) with a good yield, and the reaction liquid can be employed as it is for the subsequent step. If necessary, by means of subjecting the reaction liquid to a conventional purification measure such as distillation, extraction, washing, solvent evaporation, and column or thin-layer chromatography, the compound of formula (VII) can be isolated and purified.

Examples of 2-halomethylaziridine as a synthesis material used in the above reaction include 2-chloromethylaziridine, 2-bromomethylaziridine and 2-iodomethylaziridine. These compounds can be easily synthesized from allylamine on the market in accordance with the method mentioned in the following Examples 1 or 2.

Step (b)

In this step, 1-azabicyclo[1.1.0]butane of formula (VII) obtained in the above step (a) is made to react with a carboxylic acid, and the resultant compound is subjected to solvolysis, and, thus, is converted into 3-hydroxyazetidine of formula (IV).

In this reaction, the compound of formula (VII) is firstly dissolved in a reactionally inert solvent like ether type solvent such as diethyl ether and tetrahydrofuran which are mentioned in the above step (a), and, then, a carboxylic acid is added to the resultant solution, and the mixture is stirred.

The aforementioned carboxylic acid may be appropriately selected from among formic acid and the organic acids which are mentioned above as forming acid addition salts of the compound of formula (I). Especially preferable are formic acid and acetic acid.

The amount of the carboxylic acid used in this reaction is not especially restricted. Usually, the carboxylic acid is used at the proportion of about 1 to about 20 moles, preferably about 1.5 to about 5 moles, per mole of the compound of formula (VII). The reaction temperature is not strictly limited, and may be adequately changed according to the species and amount of the carboxylic acid used. Usually, the reaction is suitably carried out at a temperature in the range of about −78° C. to about 100° C., preferably about −78° C. to about 60° C., and, under such conditions, the reaction can be completed in about 10 minutes to several days.

The reaction is preferably conducted in the stream of inert gas such as nitrogen or argon gas.

Next, the compound obtained by the above reaction is subjected to solvolysis such as hydrolysis, and, thus, there can be produced 3-hydroxyazetidine of formula (IV).

Said solvolysis reaction is conducted by treating the compound obtained from the above reaction either in water or in alcohol type solvent such as methanol, ethanol and isopropanol or in a mixed solvent composed of water and organic solvent such as acetonetrile, tetrahydrofuran and dioxane, and in the presence of suitable base or inorganic acid such as hydrochloric acid, sulfuric acid, hydrobromic acid and hydroiodic acid which are mentioned in the above step (a), at a temperature in the range of about −20° C. to about 50° C., preferably at a comparatively as low as about 0° to a room temperature, for about 10 minutes to several hours.

If necessary, the reaction liquid obtained by the above step may be subjected to a conventional purification measure such as extraction, washing, solvent evaporation, column or thin-layer chromatography or recrystallization, and then the desired compound of formula (IV) can be isolated and purified. However, without such isolation step, the reaction liquid can be employed as it is for the subsequent step.

Step (c)

In this step, 3-hydroxyazetidine of formula (IV) obtained in the above step (b) is converted into 3-hydroxy-1-(1,3-thiazolin-2-yl)azetidine of formula (III).

This step can be conducted by either the method (i) or (ii) as follows:

(i) The above conversion is carried out by stirring 3-hydroxyazetidine of formula (IV) together with a 2-substituted thiazoline derivative represented by the following formula (V)

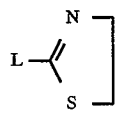

(V)

wherein L denotes a leaving group in the above-mentioned reaction ally inert solvent, preferably alcohol type solvent such as methanol or ethanol, and, preferably, in the presence of the above-mentioned suitable base such as sodium hydrogencarbonate, potassium hydrogencarbonate, sodium carbonate or potassium carbonate.

Examples of the leaving group denoted by the mark L in the compounds of the above formula (V) include azido group; halogen atoms such as chlorine, bromine and fluorine; lower alkanoyloxy groups such as acetoxy and propionyloxy; sulfonyloxy groups such as benzenesulfonyloxy, tosyloxy and methanesulfonyloxy; lower alkoxy groups such as methoxy and ethoxy; and lower alkylthio groups such as methylthio and ethylthio. Especially preferable among these are lower alkylthio groups.

The amount of the base and the compound of formula (V) used in this reaction is not especially restricted. Usually, the base and the compound of formula (V) are each used at the proportion of about 1 to about 3 moles, preferably about 1 to about 1.5 mole, per mole of the compound of formula (IV). The reaction temperature is not strictly limited, and may be adequately changed according to the species and amount of the solvent, the base and the compound of formula (V) used. Usually, however, the reaction is suitably carried out at a temperature in the range of a room temperature to about 100° C., preferably a room temperature to about 80° C., and, under such conditions, the reaction can be completed in about 1 to about 24 hours.

The reaction is preferably conducted in the stream of inert gas such as nitrogen or argon gas.

(ii) The conversion from the compound of formula (IV) into the compound of formula (III) can also be carried out by stirring the compound of formula (IV) together with haloethylisothiocyanate in the above-mentioned suitable solvent, preferably in acetonitrile, and, preferably, in the presence of the above-mentioned organic base such as triethylamine.

Examples of the haloethylisothiocyanate used here as a raw material include chloroethylisothiocyanate, bromoethylisothiocyanate and iodoethylisothiocyanate.

The amount of the base and the haloethylisothiocyanate used in this reaction is not especially restricted. Usually, however, the base and the haloethylisothiocyanate are each used at the proportion of about 1 to about 3 moles, preferably about 1 to about 1.5 mole, per mole of the compound of formula (IV). The reaction temperature is not strictly limited, and may be adequately changed according to the species and amount of the base and haloethylisothiooyanate. Usually, however, the reaction is suitably carried out at a temperature in the range of about −20° C. to about 50° C., preferably comparatively as low as about 0° C. to a room temperature, and, under such conditions, the reaction can be completed in about 10 minutes to several hours.

The reaction is preferably conducted in the stream of inert gas such as nitrogen or argon gas.

Whichever method (i) or (ii) is carried out, the reaction liquid may be subjected to a conventional purification measure such as extraction, washing, solvent evaporation, column or thin-layer chromatography or recrystallization if need be, and then the compound of formula (III) can be isolated and purified. Moreover, also when stirred together with the organic and inorganic acids which are mentioned above as forming acid addition salts of the compound of formula (I) in a suitable solvent, the compound of formula (III) can be isolated as an acid addition salt.

The compound of formula (III) prepared in the above manner is a novel compound which has never been mentioned in any other literatures, and constitutes a part of the present invention.

Step (d)

In this step, 3-hydroxy-1-(1,3-thiazolin-2-yl)azetidine of formula (III) obtained in the above step (c) is converted into 3-mercapto-1-(1,3-thiazolin-2-yl)azetidine derivatives of formula (II).

This step can be conducted by either the method (i) or (ii) as follows:

(i) The above conversion can be carried out by activating the hydroxyl group of the compound of formula (III), and, thereafter, by making the resultant activated derivative react with a compound represented by formula RSH (wherein R is as defined above) or with its salt.

Examples of the thiol compound represented by formula RSH include thioacetic acid, thiopropionic acid, thiobenzoic acid, t-butylmercaptan, benzylmercaptan, benzhydrylmercaptan, tritylmercaptan, benzylmercaptan whose phenyl group is substituted with one or two hydroxy, methoxy, acetoxy or nitro, phenylmercaptan which may be substituted with lower alkyl group, nitro group or halogen atom, or naphthyl mercaptan. Preferable among these are thiol compounds whose R denotes lower alkanoyl group or substituted or unsubstituted benzoyl group. Furthermore, this thiol compound may take the form of a salt with alkaline metal such as sodium and potassium.

The reaction to activate the hydroxyl group of the compound of formula (III) can be conducted by allowing the compound of formula (III) to react with an hydroxyl group-activating reagent like organic sulfonylhalide such as methanesulfonyl chloride and 4-toluenesulfonyl chloride or acylhalide such as acetylchloride in the above-mentioned inert solvent like ether type solvent such as diethylether and tetrahydrofuran, and, preferably in the presence of the above-mentioned suitable base like organic bases such as triethylamine, diisopropylethylamine and N,N-dimethylaminopyridine, or a combination thereof.

The amount of the base and the hydroxyl group-activating reagent used in this reaction is not especially restricted. Usually, however, the base and the activating reagent are each used at the proportion of about 1 to about 3 moles, Preferably about 1 to about 1.5 mole, per mole of the compound of formula (III). The reaction temperature is not strictly limited, and may be adequately changed according to the species and amount of the base and the activating reagent. Usually, however, the reaction is suitably carried out at a temperature in the range of about −20° C. to about 50° C., preferably comparatively as low as about 0° C. to a room temperature, and, under such conditions, the reaction can be completed in about 10 minutes to several hours.

The reaction is preferably conducted in the stream of inert gas such as nitrogen or argon gas.

Then, the compound of formula (III) whose hydroxyl group has been activated is stirred together with the above compound represented by formula RSH or its salt in the above-mentioned suitable solvent such as dimethylformamide, and, thus, there can be obtained the desired compounds of formula (II) intended in this step.

The amount of the thiol compound represented by formula RSH or its salt used in this reaction is not especially restricted. Usually, however, the compound or its salt is used at the proportion of about 1 to about 8 moles, preferably about 1 to about 6 moles, per mole of the compound whose hydroxyl group has been activated. The reaction temperature is not strictly limited, and may be adequately changed according to the species and amount of the thiol compound or its salt. Usually, however, the reaction is suitably carried out at a temperature in the range of about 0° C. to about 150° C., preferably a room temperature to about 120° C., and, under such conditions, the reaction can be completed in about 10 minutes to several hours.

The reaction is preferably conducted in the stream of inert gas such as nitrogen or argon gas.

(ii) The conversion of the compound of formula (III) to the compounds of formula (II) can be also conducted by making the compound of formula (III) react with di(lower) alkylazodicarboxylate, triphenylphosphine and the above compound represented by RSH.

Examples of di(lower)alkylazodicarboxylate used here include diethylazodicarboxylate and diisopropylazodicarboxylate. As for the compound represented by RSH, there can be employed those mentioned in the above (i).

The reaction can be carried out by stirring the compound of formula (III) together with di(lower)alkylazodicarboxylate, triphenylphosphine and the compound represented by RSH in the above-mentioned suitable solvent like ether type solvent such as diethylether and tetrahydrofuran.

The amount of the di(lower)alkylazodicarboxylate, triphenylphosphine and the compound represented by RSH used in this reaction is not especially restricted. Usually, however, these compounds are each used at the proportion of about 1 to about 3 moles, preferably about 1 to about 2 moles, per mole of the compound of formula (III). The reaction temperature is not strictly limited, and may be adequately changed according to the species and amount of the reagent and compounds. Usually, however, the reaction is suitably carried out at a temperature in the range of about −20° C. to about 50° C., preferably about 0° C. to a room temperature, and, under such conditions, the reaction can be completed in about 10 minutes to several hours.

The reaction is preferably conducted in the stream of inert gas such as nitrogen or argon gas.

Whichever method (i) or (ii) is carried out, the reaction liquid may be subjected to a conventional purification measure such as extraction, washing, solvent evaporation, column or thin-layer chromatography or recrystallization if need be, and then the compounds of formula (II) can be isolated and purified. Moreover, also when stirred together with the above-mentioned organic acids or inorganic acids in a suitable solvent, the compounds of formula (II) can be isolated in the form of adequate acid addition salts.

Thus obtained compounds of formula (II) are also novel compounds which have never been mentioned in any other literatures, and constitute a part of the present invention.

Step (e)

In this step, 3-mercapto-1-(1,3-thiazolin-2-yl)azetidine derivatives of formula (II) or its acid addition salts obtained in the above step (d) are converted, by means of cleaving off the group R therefrom, into 3-mercapto-1-(1,3-thiazolin-2-yl)azetidine of formula (I) or its acid addition salts of the present invention.

The group R can be cleaved off from the compounds of formula (II) by means of the above-mentioned solvolysis reaction such as hydrolysis, or by the following hydrogenolysis reaction.

Hydrogenolysis can be conducted by treating the compounds of formula (II) in, for example, a buffer solution of pH 5–7 such as an acetate buffer solution, a morpholinopropanesulfonate-sodium hydroxide buffer solution or a phosphate buffer solution; a mixed solvent composed of these buffer solutions and alcoholic solvent; or in a mixed solvent such as tetrahydrofuran-water, tetrahydrofuran-ethanol-water, dioxane-water, dioxane-ethanol-water and n-butanol-water each containing dipotassium phosphate, sodium bicarbonate, and the like; with use of hydrogen of about 1 to 4 atm, in the presence of a hydrogenation catalyst such as platinum oxide, palladium-activated carbon or palladium hydroxide-activated carbon, at a temperature in the range of about 0° C. to about 50° C., for about 0.25 to about 5 hours.

The above step gives the compound of formula (I) of the present invention with a good yield. The reaction liquid may be subjected to a conventional purification measure such as extraction, washing, solvent evaporation, column or thin-layer chromatography or recrystallization if need be, and then the compound of formula (I) can be isolated and purified.

Process variant B:

In the secondarily proposed process, the compound of formula (I) is produced from the compound of formula (VII), which can be prepared by the above-mentioned manner from 2-halomethylaziridine, by the reaction path shown in the following Scheme (B).

Scheme (B)

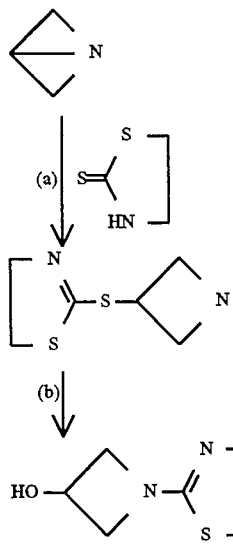

In the following, the method shown in Scheme (B) is minutely explained in accordance with each step:

Step (a)

In this step, 2-(azetidin-3-ylthio)-1,3-hiazoline of formula (VI) is produced by making 1-azabicyolo[1.1.0]butane of formula (VII) react with 1,3-thiazolidine-2-thione.

This reaction can be conducted by stirring 1-azabicyclo [1.1.0]butane of formula (VII) and 1,3-thiazolidine-2-thione in the above-mentioned suitable solvent, preferably in tetrahydrofuran, and preferably in the presence of the above-mentioned suitable base like alkaline metal hydride such as sodium hydride or alkaline metal alkoxide such as sodium methoxide.

The amount of 1,3-thiazolidine-2-thione and the base used in this reaction is not especially restricted. Usually, however, they are each used at the proportion of about 1 to about 3 moles, preferably about 1 to about 1.5 mole, per mole of 1-azabicyclo[1.1.0]butane of formula (VII). The reaction temperature is not strictly limited, and may be adequately changed according to the species and amount of 1,3-thiazolidine-2-thione and the base. Usually, however, the reaction is suitably carried out at a temperature in the range of about −78° C. to about 100° C., preferably −78° C. to a room temperature, and, under such conditions, the reaction can be completed in about 1 hour to about 24 hours.

The reaction is preferably conducted in the stream of inert gas such as nitrogen or argon gas.

The above step gives the compound of formula (VI) with a good yield. The reaction liquid may be subjected to a conventional purification measure such as extraction, washing, solvent evaporation, column or thin-layer chroma- tography or recrystallization if need be, and then the compound of formula (VI) can be isolated and purified. Moreover, when stirred together with the above organic or inorganic acid in a suitable solvent, the compound of formula (VI) can be isolated as a suitable acid addition salt.

The obtained compound of formula (VI) is a novel compound which has never been mentioned in any other literatures, and constitutes a part of the present invention.

Step (b)

In this step, 2-(azetidin-3-ylthio)-1,3-thiazoline of formula (VI) obtained in the above step (a) is treated with acid, and, thus, is converted into 3-mercapto-1-(1,3-thiazolin-2-yl)azetidine of formula (I) in accordance with the present invention.

This reaction can be carried out by stirring the above compound of formula (VI) and an acid in the above-mentioned suitable solvent, preferably in tetrahydrofuran. Examples of the above mentioned acid include the organic and inorganic acids which are mentioned above as forming acid addition salt of the compound of formula (I). Preferably used among them are lower alkylsulfonic acids such as methylsulfonic acid, The amount of acid used in this reaction is not especially restricted. Usually, however, it is used at the proportion of about 0.1 to about 3 moles, preferably about 0.1 to about 1 mole, per mole of the compound of formula (VI). The reaction temperature is not strictly limited, and may be adequately changed according to the species and amount of the acid. Usually, however, the reaction is suitably carried out at a temperature in the range of a room temperature to about 100° C., preferably a room temperature to about 80° C., and, under such conditions, the reaction can be completed in about 10 minutes to about several hours.

The reaction is preferably conducted in the stream of inert gas such as nitrogen or argon gas.

The above step gives the compound of formula (I) with a good yield. The reaction liquid may be subjected to a usual purification measure such as extraction, washing, solvent evaporation, column or thin-layer chromatography or recrystallization if need be, and then the compound of formula (I) can be isolated and purified.

Process variant C:

In the thirdly proposed process, the compound of formula (I) is produced from the compound of formula (VII), which can be prepared by the above-mentioned manner from 2-halomethylaziridine, by the reaction path shown in the following Scheme (C).

Scheme (C)

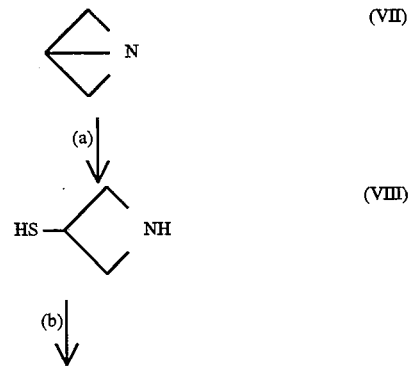

-continued
Scheme (C)

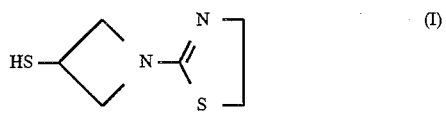

In the following, the method shown in Scheme (C) is minutely explained in accordance with each step.

Step (a)

In this step, 1-azabicyclo[1.1.0]butane of formula (VII) is converted into 3-mercaptoazetidine of formula (VIII).

The above reaction can be carried out by stirring the compound of formula (VII) together with the aforementioned compound represented by formula RSH or its salts in such a suitable solvent as mentioned above, and, then, cleaving off the group R from the resultant compound.

Examples of the compound represented by formula RSH or its salts include the above-mentioned compounds. Preferably used among these are compounds whose R denotes a lower alkanoyl group or a substituted or unsubstituted benzoyl group, or salts thereof with sodium and potassium.

The amount of the compound RSH used in this reaction with the compound of formula (VII) is not especially restricted. Usually, however, it is used at the proportion of about 1 to about 5 moles, preferably about 1 to about 3 moles, per mole of the compound of formula (VII). The reaction temperature is not strictly limited, and may be adequately changed according to the species and amount of the compound RSH. Usually, however, the reaction is suitably carried out at a temperature in the range of about −78° C. to about 80° C., preferably −50° C. to a room temperature, and, under such conditions, the reaction can be completed in about 10 minutes to several hours.

The reaction is preferably conducted in the stream of inert gas such as nitrogen or argon gas.

Next, the reaction to cleave off the group R from the compound obtained in the above reaction can be carried out in accordance with the method shown in step (e) of the above process variant A.

Incidentally, when the above reaction is conducted with use of a thiol compound whose R is acyl group as a starting material, there is added a group R in two molar equivalents to the compound of formula (VII) under circumstances (See: Example 9 which is mentioned later). In this case, however, the group R can also be cleaved off in accordance with the method shown in step (e) of the above process variant A (See: Example 10 which is mentioned later).

The above step gives the compound of formula (VIII) with a good yield. The reaction liquid may be subjected to a conventional purification measure such as extraction, washing, solvent evaporation, column or thin-layer chromatography or recrystallization if need be, and then the compound of formula (VIII) can be isolated and purified. Moreover, when stirred together with the above organic or inorganic acid in a suitable solvent, the compound of formula (VIII) can be isolated as a suitable acid addition salt.

Step (b)

In this step, the compound of formula (VIII) obtained in the above step (a) is made to react with the above mentioned 2-substituted-3-thiazoline derivatives of formula (V), and, thus, there is produced the compound of formula (I) in accordance with the present invention.

This step can be conducted in the same manner as the method (i) or (ii) of step (c) in the above process variant A.

Whichever method (i) or (ii) is employed, the reaction liquid may be subjected to a conventional purification measure such as extraction, washing, solvent evaporation, column or thin-layer chromatography or recrystallization if need be, and then the compound of formula (I) can be isolated and purified.

When stirred together with the above organic of inorganic acid in a suitable solvent, the compound of formula (I) which is obtained by the above process variants A to C can be isolated in the form of acid addition salts. Among thus obtained acid addition salts, the salt with inorganic acid, especially hydrochloric acid, can easily be obtained in the form of crystal having excellent storage stability as shown in Examples stated below, and is quite useful as a synthesis intermediate for long-period storage.

In the above stated manner, there can be produced 3-mercapto-1-(1,3-thiazolin-2-yl)azetidine of formula (I) or its acid addition salts which is intended in the present invention.

As stated concretely in Example 13 mentioned below, when Scheme (D) mentioned below is followed with use of the compound of formula (I) which is provided by the present invention, there can be obtained, with good yield, the carbapenem compound of formula (IX) which has excellent antibacterial activity and which becomes orally administrable when esterified.

Scheme (D)

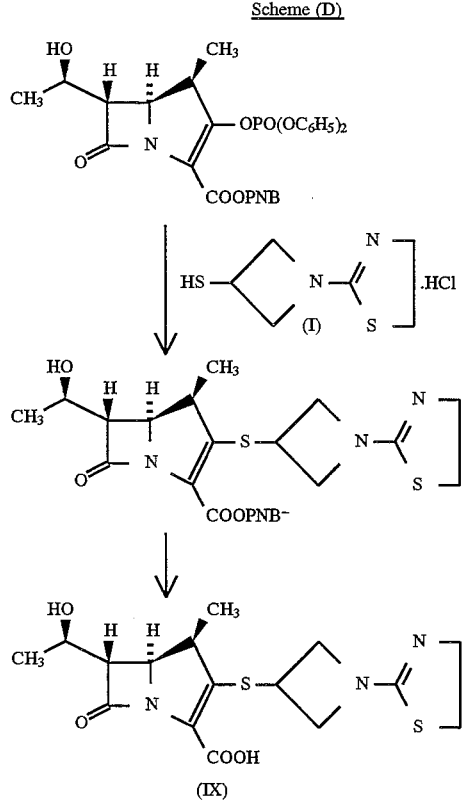

In the following, this invention is more detailedly explained by Examples, Production Examples and Experimental Examples. This invention is, however, not restricted at all by the following descriptions.

Incidentally, the marks in the descriptions have the following meanings:

Ac: acetyl

PNB: p-nitrobenzyl

EXAMPLE 1

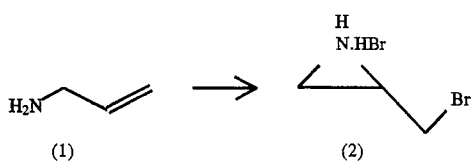

In 94 ml of bromine solution dissolved in 110 ml of diethylether, there was added 80 g of allylamine (1) dropwise at a temperature of 15° C. or less, and was stirred for a day at a room temperature. After the reaction was over, the crystal which had deposited was taken out by filtration, and was washed with 55 ml of diethylether, and, then, was subjected to vacuum drying, and, thus, there was obtained 302.6 g (yield: 99.6%) of 2-bromomethylaziridine hydrobromide (2).

$^1$H-NMR (CD$_3$OD) δ: 3.35 (dd, 1H, J=9.89 Hz, 14.19 Hz), 3.71 (dd, 1H, J=3.30 Hz, 14.19 Hz), 3.86 (dd, 1H, J=8.58 Hz, 10.89 Hz), 4.01 (dd, 1H, J=4.62 Hz, 10.89 Hz), 4.4–4.6 (m, 1H)

EXAMPLE 2

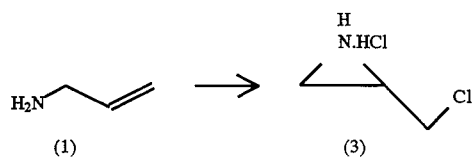

A 900 ml dried solution of dichloromethane containing 9.64 ml of sulfuryl chloride and a catalytic amount of iodine dissolved therein was subjected to reflux at 40° C., and, to this solution, there was added dropwise a 100 ml dried solution of dichloromethane containing 7.6 ml of allylamine (1) dissolved therein, and, after the addition was over, the solution was stirred at the same temperature for two hours. After the reaction was over, the reaction liquid was left still until it had a room temperature, and, then, a residue which was obtained by filtration was washed with dichloromethane and n-hexane, and, next, was subjected to vacuum drying, and, thus, there was obtained 8.37 g (yield: 65.8%) of 2-chloromethylaziridine hydrochloride (3).

$^1$H-NMR (D$_2$O) δ: 3.26 (dd, 1H, J=9.57 Hz, 13.85 Hz), 3.53 (dd, 1H, J=3.30 Hz, 13.85 Hz), 3.78 (dd, 1H, J=6.60 Hz, 12.21 Hz), 3.88 (dd, 1H, J=4.95 Hz, 12.21 Hz), 4.38–4.47 (m, 1H)

EXAMPLE 3

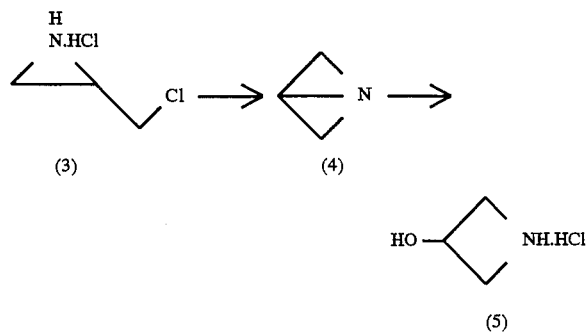

A 25 ml suspension of tetrahydrofuran containing 1.28 g of 2-chloromethylaziridine hydrochloride (3) obtained in the above Example 2 was stirred in the atmosphere of nitrogen at −78° C., and, to this solution, 21 mmol of n-butyllithium was added dropwise over a period of five minutes. After the addition was over, the solution was stirred at the same temperature for one hour, and, while left still so that it might have a room temperature, the solution was further stirred for 10 minutes. To the reaction liquid, there was added 2 ml of 50% aqueous solution of potassium hydroxide, and was stirred for 10 minutes. Thereafter, the reaction liquid was distilled under normal pressure, and, thus, there was obtained 1-azabicyclo[1.1.0]butane (4) having a boiling point of about 51° C. The obtained distillate was dried with potassium hydroxide and potassium carbonate, and, then, was cooled to −40° C, and, to the distillate, there was added dropwise a solution of 5 ml tetrahydrofuran containing 1.13 ml of formic acid. The resultant solution was left still until it had a room temperature, and, then, was further stirred for 18 hours, and, next, the solvent was condensed under reduced pressure, and, to this solution, there was added 16 μl methanol solution containing 60 mmol of concentrated hydrochloric acid at 0° C., and, subsequently, the solution was stirred for 20 hours. After the reaction was over, the solvent was evaporated in a vacuum, and, thus, there was obtained 570 mg (yield: 52.0%) of 3-hydroxyazetidine hydrochloride (5) in the form of colorless needle crystal.

$^1$H-NMR (D$_2$O) δ: 4.0–4.3 (m, 2H), 4.1–4.3 (m, 2H), 4.6–4.8 (m, 1H)

EXAMPLE 4

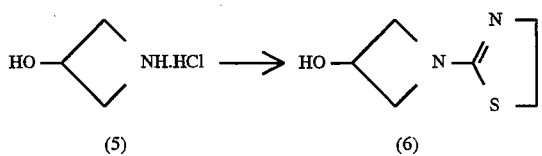

(i) To a 73 ml solution of methanol anhydride containing 7.95 g of 3-hydroxyazetidine hydrochloride (5) obtained in the above Example 3, there was added 5.09 g of potassium hydrogencarbonate at a room temperature, and, then, there was added 9.67 g of 2-(methylthio)-1,3-thiazoline dropwise, and, then, the resultant solution was subjected to heating and reflux for 20 hours. After the reaction liquid was left still until it had a room temperature, 3.63 g of potassium hydrogencarbonate was further added, and the liquid was stirred for one hour at the same temperature. After the reaction was over, precipitate was removed by filtration, and the solvent was evaporated in a vacuum, and, to the obtained residue, there was added 100 ml of tetrahydrofuran, and the resulting mixture was stirred for one hour at a room temperature. Insoluble matters were removed by filtration, and the solvent was evaporated in a vacuum, and, then, the residue was subjected to silica gel column chromatography (eluent: chloroform-methanol), and, thus, there was obtained 8.23 g (yield: 71.5%) of 3-hydroxy-1-(1,3-thiazolin-2-yl)azetidine (6) in the form of colorless crystal.

$^1$H-NMR (CDCl$_3$) δ: 3.356 (t, 2H, J=7.26 Hz), 3.70~4.00 (m, 4H), 4.211 (t, 2H, J=8.21 Hz), 4.622~4.705 (m, 1H), 4.971 (s, 1H)

(ii) A 1.5 ml solution of acetonitrile anhydride containing 219 mg of 3-hydroxyazetidine hydrochloride (5) was cooled to 0° C. in the stream of nitrogen, and, to this solution, there were added 0.31 ml of triethylamine and subsequently a 0.3 ml solution of acetonitrile anhydride containing 250 mg of chloroethylisothiocyanate dissolved therein, and the resultant solution was stirred for 30 minutes at the same temperature, and, after left still until it had a room temperature, the solution was further stirred for two hours. Next, dichloromethane was added to the reaction liquid, and the resultant solution was washed with a saturated aqueous solution of potassium carbonate, and, thereafter, the dichloromethane layer was dried with magnesium sulfate, and then was condensed under reduced pressure, and, thus, there was obtained 300 mg (yield: 95%) of 3-hydroxy-1-(1,3-thiazolin-2-yl)azetidine (6) in the form of colorless needle crystal.

The NMR spectrum of this product was utterly identical with that of the product obtained in the above (i).

EXAMPLE 5

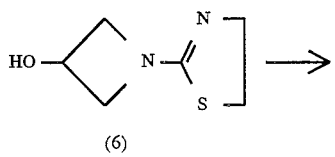

(6)

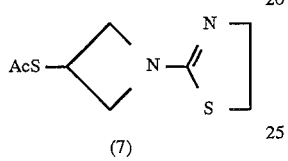

(7)

(i) To 2 ml suspension of tetrahydrofuran anhydride containing 790 mg of 3-hydroxy-1-(1,3-thiazolin-2-yl) azetidine (6) obtained in the above Example 4, there was added 6 mg of N,N-dimethylaminopyridine while the suspension was cooled with ice, and, subsequently, there were added dropwise 557 mg of triethylamine and 575 mg of mesyl chloride while the suspension was cooled with ice, and the resulting mixture was stirred for 40 minutes at the same temperature. After the reaction was over, the solvent was evaporated in a vacuum, and, to the resultant residue, there was added ethyl acetate, and the resultant mixture was washed with a saturated aqueous solution of sodium hydrogencarbonate. Then, the resultant aqueous layer was further extracted with ethyl acetate. After the obtained organic layer was dried with magnesium sulfate, the solvent was evaporated in a vacuum, and the residue was subjected to silica gel column chromatography (eluent: chloroform-methanol), and, thus, there was obtained 995 mg (yield: 84.3%) of 3-mesyloxy-1-(1,3-thiazolin-2-yl)azetidine in the form of colorless crystal.

$^1$H-NMR (CDCl$_3$, 270 MHz, ppm) δ: 3.07 (s, 3H), 3.39 (t, 2H, J=7.6 Hz), 4.03 (t, 2H, J=7.6 Hz), 4.14–4.19 (m, 2H), 4.37–4.31 (m, 2H), 5.28–5.33 (m, 1H)

Next, to a 1 ml solution of dimethylformaide anhydride containing 118 mg of 3-mesyloxy-1-(1,3-thiazolin-2-yl) azetidine obtained from the above reaction, there was added 228 mg of potassium thioacetate at a room temperature, and the mixture was stirred at 80° C. for four hours. After the reaction was over, the solvent was evaporated in a vacuum, and, then, after ethyl acetate was added, the solution Was washed with a saturated aqueous solution of potassium hydrogencarbonate, and, then, the aqueous layer was subjected to back extraction with ethyl acetate. The obtained organic layer was dried with magnesium sulfate, and the residue was subjected to silica gel column chromatography (eluent: chloroform), and, thus, there was obtained 88 mg (yield: 81.2%) of 3-acetylthio-1-(1,3-thiazolin-2-yl)-azetidine (7) in the form of light-yellowish oily matter.

$^1$H-NMR (CDCl$_3$) δ: 2.333 (s, 3H ), 3.352 (t, 2H, J=7.26 Hz), 3.885 (dd, 2H, J=8.24, 5.28 Hz), 4.012 (t, 2H, J=7.26 Hz), 4.250–4.374 (m, 1H), 4.426 (t, 2H, J=8.25 Hz)

(ii) There were added 119 mg of 3-hydroxy-1-(1,3-thiazolin-2-yl)azetidine (6) and two molar equivalents of thioacetic acid, while cooled with ice, to 10 ml of tetrahydrofuran solution containing two molar equivalents of triphenylphosphine and two molar equivalents of diethylazodicarboxylate, and the resultant solution was stirred for one hour at the same temperature, and for further one hour at a room temperature. The solvent of the reaction liquid was evaporated in a vacuum, and the obtained residue was subjected to silica gel column chromatography (eluent: chloroform-ethanol), and, thus, there was obtained 107 mg (yield: 65%) of 3-acetylthio-1-(1,3-thiazolin-2-yl)azetidine (7).

The NMR spectrum of this product was utterly identical with that of the product obtained in the above (i).

EXAMPLE 6

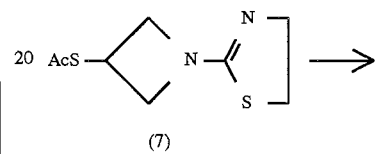

(7)

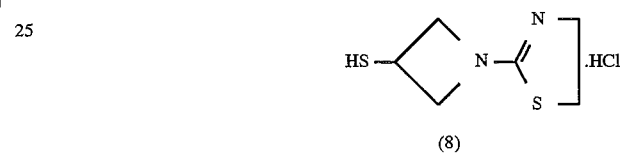

(8)

There was dissolved 12.98 g of 3-acetylthio-1-(1,3-thiazolin-2-yl)azetidine (7) obtained in the above Example 5 into 58.3 ml of isopropylalcohol, and to the resultant solution which was being cooled with ice, there was added 37.3 ml solution (1.69N) of potassium hydroxide dissolved in methanol, and the resultant solution was stirred for 10 minutes. Then, at the same temperature, 66 ml solution (2N) of hydrochloric acid in methanol was added to the above solution so that it might be quenched, and, after the resultant mixture was stirred for 15 minutes at a room temperature, insoluble matters were removed by filtration. The residue obtained by condensing the filtrate was dissolved in 39 ml of isopropylalcohol, and, after insoluble matters were removed by filtration, the filtrate was condensed. To the obtained residue, there was added 58.5 ml of n-butanol so that the residue might be condensed, and, thus, there was obtained 3-mercapto-1-(1,3-thiazolin-2-yl)azetidine hydrochloride (8) in the form of yellowish white solid.

To this solid, there was added 22.8 ml of acetonitrile, and the resulting mixture was stirred at a room temperature for 15 minutes so that the mixture might be dissolved, and, then, 113.4 ml of acetone was added dropwise over a period of 30 minutes. Then, further 113.4 ml of acetone was added dropwise over a period of 15 minutes, and, then, the resultant solution was stirred for 30 minutes while cooled with ice. The solid which was deposited was taken by filtration, and then was washed with 150 ml of acetone, and next was dried for a day under reduced pressure, and, thus, there was obtained 10.41 g (purity: 97.5%; yield: 80.3%) of 3-mercapto-1-(1,3-thiazolin-2-yl)azetidine hydrochloride (8) in the form of colorless needle crystal.

$^1$H-NMR (CDCl$_3$) δ: 2.57 (d, 1H, J=8.2 Hz), 3.59 (t, 2H, J=7.4 Hz), 4.02–4.18 (m, 4H), 4.63 (t, 2H, J=7.4 Hz), 5.19–5.26 (m, 1H), 12.19 (s, 1H)

This product was confirmed as a crystal by means of polarizing-microscopic observation. Besides, in powder

17

X-ray diffraction pattern, there was shown a characteristic peak at each of the following lattice spacing (d) (unit: Å)

7.32, 5.96, 5.04, 5.00, 4.90, 4.44, 4.23, 4.08, 3.79, 3.71, 3.66, 3.29, 3.14, 3.10, 2.98, 2.91, 2.82, 2.55, 2.50

Incidentally, both the above crystal filtrate and the acetone washings were condensed, and the resulting residue was dissolved in 10 ml of n-butanol and then was re-condensed, and, next, was dried under reduced pressure for one day. To the obtained 1.7 g of orange solid, there was added 1.7 ml of acetonitrile, and the resulting mixture was stirred for 15 minutes at a room temperature so that it might be dissolved, and, to the resulting solution, there was added 17 ml of acetone dropwise over a period of 15 minutes, and the solution was stirred for 30 minutes while cooled with ice, and, thus, there was obtained 1.2 g (purity: 89.3%; yield: 8.5%) of 3-mercapto-1-(1,3-thiazolin-2-yl)azetidine hydrochloride (8) in the form of colorless needle crystal.

EXAMPLE 7

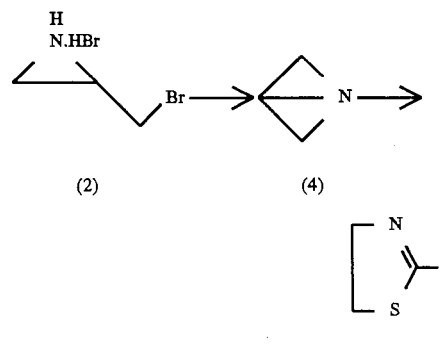

To a 12 ml suspension of dried tetrahydrofuran containing 1.00 g of 2-bromomethylaziridine hydrobromide (2) obtained in the above Example 1, there was added dropwise 5.94 ml (1.63M) of of n-butyllithium at −78° C., and the resulting mixture was stirred for one hour. The reaction liquid was distilled under normal pressure in a water bath (90° C.), and each of the evaporated fraction was taken out, and, thus, there was obtained a solution of 1-azabicyclo [1.1.0]butane (4) dissolved in tetrahydrofuran.

To a 5 ml solution of dried tetrahydrofuran containing 550 mg (4.61 mmol) of 1,3-thiazoline-2-thione which was being cooled with ice, on the other hand, there was added 181 mg (55%) of sodium hydride, and the resulting mixture was stirred for one hour. To the obtained solution, there was added dropwise the above solution of 1-azabicyclo[1.1.0] butane dissolved in tetrahydrofuran at −78° C., and the resulting solution was stirred at a room temperature for 20 hours, and, then, the reaction liquid was subjected to high performance liquid chromatography, and, thus, there was obtained 2-(azetidin-3-ylthio)-1,3-thiazolidine (9).

$^1$H-NMR (CD$_3$OD) δ: 3.32 (t, 2H, J=8 Hz), 3.46 (dd, 2H, J=6 Hz, 10 Hz), 3.90 (dd, 2H, J=8 Hz, 10 Hz), 4.06 (t, 2H, J=8 Hz), 4.3–4.5 (m, 1H)

18

EXAMPLE 8

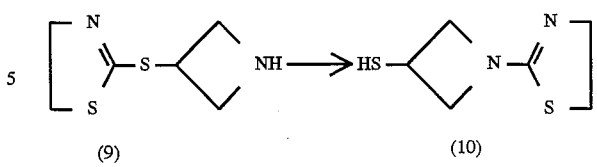

To a solution of tetrahydrofuran anhydride containing 2-(azetidin-3-ylthio)-1,3-thiazolidine (9) obtained in the above Example 7, there was added 0.329 ml of methylsulfonic acid, and, then, the solvent was condensed under reduced pressure, and, to the obtained solution, there was added methanol, and the resulting solution was subjected to heating and reflux for three hours. After the reaction was over, the solvent was distilled off, and the residue was separated and purified by high performance liquid chromatography, and, thus, there was obtained 186 mg (yield: 23.2%) of 3-mercapto-1-(1,3-thiazolin-2-yl)azetidine (10) of the present invention.

The NMR spectrum of the hydrochloride obtained by treating the above compound (10) with hydrochloric acid was utterly identical with that of the compound (8) obtained in the above Example 6.

EXAMPLE 9

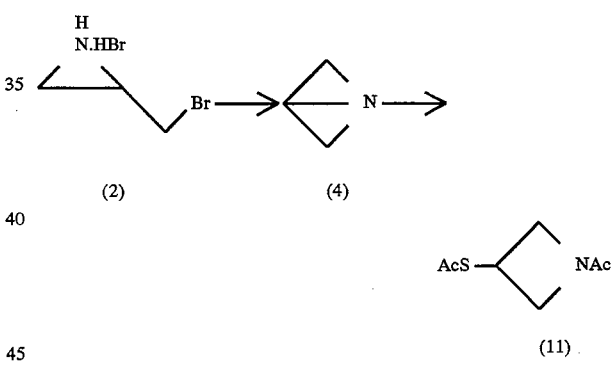

With use of 2.00 g of 2-bromomethylaziridine hydrobromide (2) obtained in the above Example 1, there was produced a solution of 1-azabicyclo[1.1.0]butane (4) dissolved in tetrahydrofuran by the same method as in the above Example 7. Next, to a 5 ml solution of dried tetrahydrofuran containing 1.32 ml of thioacetic acid, there was added dropwise a solution of compound (4) dissolved in tetrahydrofuran at a temperature of −40° C. or lower, and the resulting mixture was stirred at a room temperature for 18 hours. After the reaction was over, the solvent was distilled off, and the residue was separated and purified by silica gel column chromatography (eluent: chloroform-acetone), and, thus, there was obtained 828 mg (yield: 51.8%) of 1-acetyl-3-acetylthioazetidine (11).

$^1$H-NMR (CDCl$_3$) δ: 1.87 (s, 3H), 2.35 (s, 3H), 3.89 (dd, ½×2H, J=5 Hz, 10 Hz), 4.01 (dd, ½×2H, J=5 Hz, 9 Hz), 4.1–4.2 (m, 1H), 4.42 (t, ½×2H, J=10 Hz), 4.61 (t, ½×2H, J=10 Hz)

EXAMPLE 10

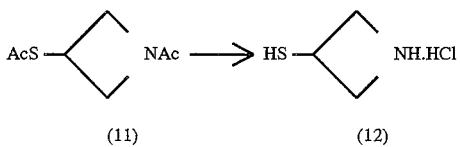

To 104 mg of 1-acetyl-3-acetylthioazetidine (11) obtained in the above Example 9, there was added 1.0 ml of 2.6N hydrochloric acid, and the resulting solution was subjected to heating and reflux for one hour. After the reaction was over, water was added, and the solution was washed with ethylacetate, and, then, the aqueous layer was evaporated in a vacuum. The obtained residue was dried in a vacuum, and, thus, there was obtained 71 mg (yield: 94.4%) of 3-meroaptoazetidine hydrochloride (12).

$^1$H-NMR (D$_2$O) δ: 4.0–4.3 (m, 3H), 4.5–4.7 (m, 2H)

EXAMPLE 11

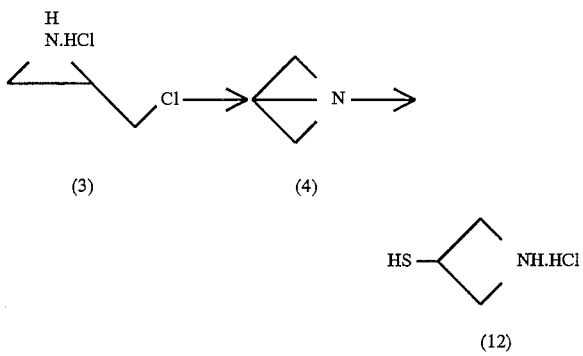

With use of 1.28 g of 2-chloromethylaziridine hydrochloride (3) obtained in the above Example 2, there was produced a solution of tetrahydrofuran containing 1-azabicyclo [1.1.0]butane (4). After this solution was dried with potassium hydroxide and potassium carbonate, there was added dropwise 0.85 ml of thioacetic acid at a room temperature. After the resulting solution was stirred for one hour at the same temperature, the reaction liquid was condensed under reduced pressure, and, then, 3.33 ml of 3N hydrochloric acid was added, and the resulting solution was subjected to heating and reflux for one hour. After the reaction liquid was left still until it had a room temperature, 30 ml of water was added thereto, and the resulting solution was washed with ethylacetate. The aqueous layer which was obtained by separation was put together with the aqueous layer which had been extracted from organic layer, and, then, the solvent was evaporated in a vacuum, and, thus, there was obtained 913 mg (yield: 72.7%) of 3-mercaptoazetidine hydrochloride (12) in the form of colorless oily matter.

The NMR spectrum of the compound (12) was utterly identical with that of the compound obtained in the above Example 10.

EXAMPLE 12

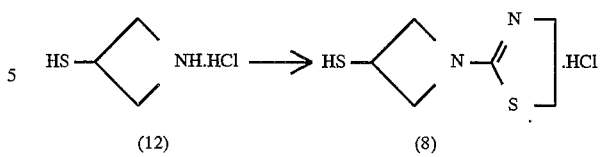

To a solution of 22.7 mg of 3-mercaptoazetidine hydrochloride (12) obtained in the above Example 11 dissolved in 95% methanol (including 1 ml of water), there were added 26.6 mg of 2-(methylthio)-1,3-thiazoline and 5.2 mg of triphenylphosphine, and the resulting solution was subjected to heating and reflux for six hours. After the reaction was over, the solvent was evaporated in a vacuum, and the obtained residue was dissolved in a 0.1N hydrochloric acid, and the resulting mixture was washed with ethylacetate. The solvent in the obtained aqueous layer was evaporated in a vacuum, and the obtained residue was separated and purified by high performance liquid chromatography, and, thus, there was produced 29.1 mg (yield: 73.4%) of 3-mercapto-1-(1,3-thiazolin-2-yl)azetidine hydrochloride (8) in the form of colorless needle crystal.

The NMR spectrum of this product was utterly identical with that of the product obtained in the above Example 6.

EXAMPLE 13

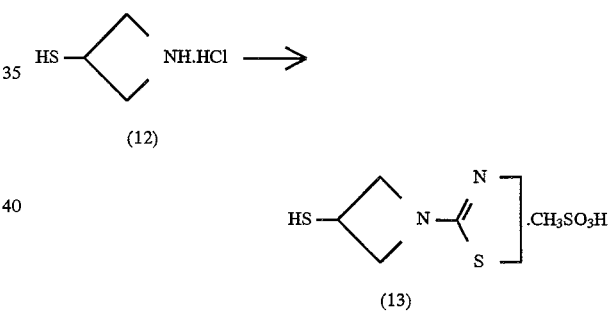

To a solution of 63.3 mg of 3-mercaptoazetidine hydrochloride (12) obtained in the above Example 10 dissolved in 1.0 ml of dried tetrahydrofuran, there was added 0.07 ml of triethylamine in the stream of nitrogen at a room temperature, and the resulting solution was stirred for 30 minutes. To this solution, there was added dropwise a solution of 70.3 mg of 2-chloroethylisothiocyanate dissolved in dried tetrahydrofuran, and the resulting solution was further stirred for one hour. After the reaction liquid was cooled to 0° C., 0.04 ml of methanesulfonic acid was added dropwise, and the resulting solution was stirred for 30 minutes, and, then, the solvent was evaporated in a vacuum. To the obtained residue, there was added 1.0 ml of dried methanol, and the resulting solution was subjected to heating and reflux for one hour, and, then, the solvent was evaporated in a vacuum. The obtained residue was separated and purified by thin-layer chromatography, and, thus, there was obtained 53.4 mg (yield: 39.2%) of 3-mercapto-1-(1,3-thiazolin-2-yl)azetidine methanesulfonate (13) in the form of colorless oily matter.

EXAMPLE 14

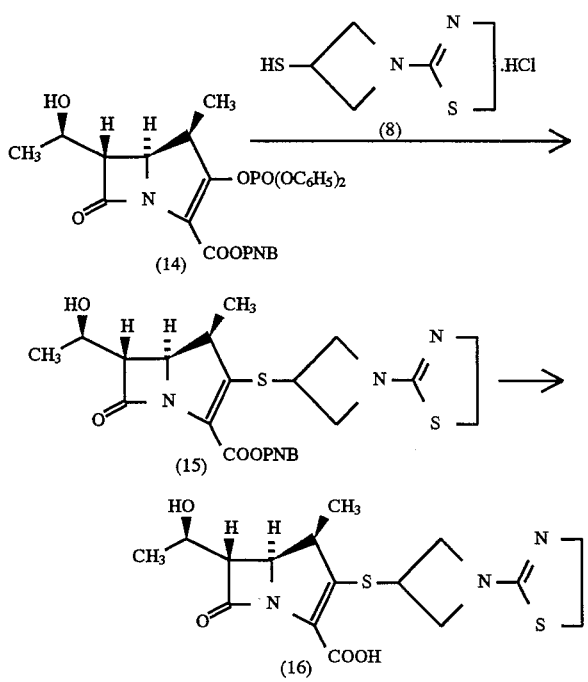

(i) There was dissolved 700 mg of 3-mercapto-1-(1,3-thiazolin-2-yl)azetidine hydrochloride (8), which was obtained in the above Example 6, in 15 ml of a mixed solvent composed of water, acetonitrile and chloroform, and, to the resulting solution, there was added 1668 mg of p-nitrobenzyl (1R,5R,6S)-2-(diphenylphosphoryloxy)-6-[(R)-1-hydroxyethyl]-1-methyl-carbapen-2-em-3-carboxylate (14). To the obtained solution which was being cooled with ice, there was added 2.8 ml of diisopropylethylamine in the stream nitrogen, and the resulting mixture was stirred at the same temperature for two hours. To the reaction liquid, there was added ethylacetate, and the resulting solution was washed with a saturated aqueous solution of sodium hydrogencarbonate and with a saturated aqueous solution of sodium chloride, and, then, the solvent was evaporated in a vacuum, and the obtained residue was subjected to silica gel column chromatography (eluent: chloroform-acetone), and, thus, there was produced 1339 mg (yield: 92%) of p-nitrobenzyl (1R,5S,6S)-2-[1-(1,3-thiazolin-2-yl)azetidin-3-yl]thio-6-[(R)-1-hydroxyethyl]-1-methyl-carbapen-2-em-3-carboxylate (15).

$^1$H-NMR (CDCl$_3$) δ: 1.235 (d, 3H, J=7.26 Hz), 1.349 (d, 3H, J=6.27 Hz), 3.160 (quintet, 1H, J=7.26 Hz), 3.265 (dd, 1H, J=2.3, 6.26 Hz), 3.367 (t, 2H, J=7.26 Hz), 3.898~4.038 (m, 4H), 4.071~4.147 (m, 1H), 4.212~4.278 (m, 2H), 4.372 (2H, J=7.92 Hz), 5.255 and 5.517 (d(AB), 2H, J=13.85 Hz), 7.665 (d, 2H, J=8.58 Hz), 8.226 (d, 2H, J=8.58 Hz)

(ii) To a solution of 1339 mg of the compound (15) obtained from the above reaction (i) which was dissolved in 20 ml of tetrahydrofuran, there were added 60 ml of 0.38M phosphate buffer solution (pH 6.0) and 11.2 g of zinc powder, and the mixture was stirred vigorously for two hours. The reaction liquid was filtrated by Celite® so that insoluble matters might be removed, and, then, the filtrate was adjusted to pH 5.5 after washed with ethylacetate. Then, the obtained solution was condensed under reduced pressure, and this condensed solution was subjected to column chromatography Diaion HP-40® (made by Mitsubishi Chemical Corporation) (eluent: 5% aqueous solution of isopropylalcohol), and, thus, there was produced 861 mg (yield: 87%) of the desired (1R,5S, 6S)-2-[1-(1,3-thiazolin-2-yl)azetidin-3-yl]thio-6-[(R)-1-hydroxyethyl]-1-methyl-carbapen-2-em-3-carboxylate (16).

$^1$H-NMR (D$_2$O) δ: 1.093 (d, 3H, J=6.93 Hz), 1.207 (d, 3H, J=6.27 Hz), 3.05~3.20 (m, 1H), 3.357 (dd, 1H, J=2.3, 5.94 Hz), 3.558 (t, 2H, J=7.26 Hz), 3.920 (t, 2H, J=7.26 Hz), 4.00~4.20 (m, 5H), 4.20~4.30 (m, 1H), 4.60~4.70 (m, 1H)

IR (KBr): 1740, 1640, 1590 cm$^{-1}$

Experimental Example 1

The 3-mercapto-1-(1,3-thiazolin-2-yl)azetidine hydrochloride (8) in the form of crystal obtained in the above Example 6 was left still in dehumidified state at a room temperature for one month. Resultantly, it was confirmed that the purity of this compound did not change at all, and that it had good storage stability.

Experimental Example 2

There was measured, by the following method, the antibacterial activity of the compound (16) which had been produced in Example 14 with use of the compound (I) of the present invention as a synthesis intermediate.

(1) Test method

There was employed the agar plate dilution method in accordance with the standard method of the Japanese Chemotherapy Society [Chemotherapy, vol. 29, 76–79 (1981)]. Concretely, a Mueller-Hinton (MH) agar liquid medium containing the test microorganism was cultured overnight at 37° C., and the resultant culture medium was diluted with a buffered saline gelatin (BSG) solution so that the concentration of the test microorganism might be about 10$^6$ cells/ml. Then, with use of a microplanter, this diluted solution was inoculated each about 5 μl on MH agar media containing the test compounds. Thus, the minimum concentration of the test compound in which no growth of the test microorganism was observed after the incubation at 37° C. for 18 hours was regarded as Minimum Inhibitory Concentration (MIC). Incidentally, all of the test organisms used here were standard strains.

(2) Results

The results of the above experiment are shown in the following Table 1.

TABLE 1

| Test organisms | MIC (μg/ml) Test compound (16) |
|---|---|
| S. aureus FDA209P JC-1 | 0.013 |
| S. aureus Terajima | ≦0.006 |
| S. aureus MS353 | ≦0.006 |
| S. pyogenes Cook | ≦0.006 |
| B. subtilis ATCC 6633 | 0.025 |
| M. luteus ATCC 9341 | 0.2 |
| E. coli NIHJ JC-2 | 0.013 |
| E. coli K-12 C600 | 0.1 |
| E. cloacae 963 | 0.05 |
| E. aerogenes ATCC 13048 | 0.1 |
| K. pneumoniae PCI-602 | 0.013 |
| S. typhimurium 11D971 | 0.025 |
| S. typhi 901 | ≦0.006 |
| S. paratyphi 1015 | 0.05 |
| S. schottmuelleri 8006 | 0.025 |
| S. enteritidis G14 | 0.39 |
| S. marcescens IAM 1184 | 0.05 |
| M. morganii IFO 3848 | 0.39 |

TABLE 1-continued

| | MIC (μg/ml) |
|---|---|
| Test organisms | Test compound (16) |
| P. mirabilis IFO 3849 | 0.39 |
| P. vulgaris OX-19 | 0.1 |
| P. vulgaris HX-19 | 0.1 |
| P. rettgeri IFO 3850 | 0.39 |

It is known from the above results that the compounds of formula (I) provided by the present invention are useful as intermediates of carbapenem compounds having excellent antibacterial activity.

What is claimed is:

1. 2-(Azetidin-3-ylthio)thiazoline represented by formula (VI) below

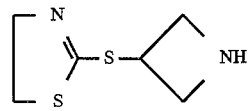   (VI)

and its acid addition salts.

2. A process to produce the compound represented by formula (VI) of claim 1 or acid addition salts thereof, which process is characterized in that 1-azabicyclo[1.1.0]butane represented by formula (VII) below

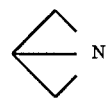   (VII)

is made to react with 1,3-thiazolidine-2-thione.

* * * * *